United States Patent [19]

Sempuku et al.

[11] Patent Number: 4,593,025

[45] Date of Patent: * Jun. 3, 1986

[54] TRIAZINE DERIVATIVES TO TREAT PAIN, FEVER, INFLAMMATION, ALLERGIES AND THROMBOSIS

[75] Inventors: Kenji Sempuku, Suita; Yoshihisa Shibata, Kameoka; Tadaaki Ohgi, Nagaokakyo, all of Japan

[73] Assignee: Nippon Shinyaku Co., Ltd., Japan

[ * ] Notice: The portion of the term of this patent subsequent to Nov. 19, 2002 has been disclaimed.

[21] Appl. No.: 744,047

[22] Filed: Jun. 12, 1985

Related U.S. Application Data

[62] Division of Ser. No. 560,445, Dec. 12, 1983, Pat. No. 4,554,275.

[30] Foreign Application Priority Data

Dec. 10, 1982 [JP] Japan .................................. 57-217529

[51] Int. Cl.$^4$ ............................................. A61K 31/53
[52] U.S. Cl. .................................................. 514/245
[58] Field of Search ......................................... 514/245

Primary Examiner—Stanley J. Friedman
Attorney, Agent, or Firm—Jacobs & Jacobs

[57] ABSTRACT

Compounds of the formula (I):

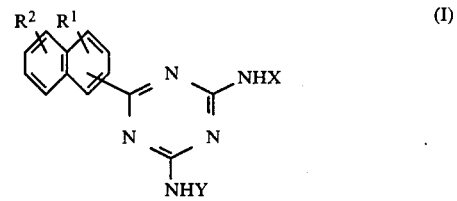

and pharmaceutically acceptable salts thereof wherein $R^1$ and $R^2$ are the same or different and each is hydrogen, hydroxy, halo, alkoxy of 1 to 4 carbon atoms or aralkyloxy of 1 to 4 carbon atoms and X and Y are each hydrogen or nicotinoyl are useful as anti-edema agents, anti-inflammatories, analgesics, anti-pyretics, anti-allergenics and anti-thrombosis agents.

12 Claims, No Drawings

TRIAZINE DERIVATIVES TO TREAT PAIN, FEVER, INFLAMMATION, ALLERGIES AND THROMBOSIS

CROSS-REFERENCE

This is a division of Ser. No. 560,445 filed Dec. 12, 1983, now U.S. Pat. No. 4,554,275.

N-nicotinoylhalogenobenzoguanamines are known in the art to exhibit strong anti-inflammatory action (see Japanese patent application No. 56-87124). It has now been discovered that triazine derivatives of the formula (I):

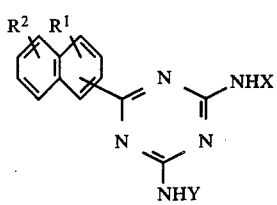

and pharmaceutically acceptable salts thereof wherein $R^1$ and $R^2$ are the same or different and each is hydrogen, hydroxy, halo, alkoxy of 1 to 4 carbon atoms or aralkyloxy of 1 to 4 carbon atoms and X and Y are each hydrogen or nicotinoyl are useful as anti-inflammatory agents and since the compounds inhibit reverse passive Aruthus reaction and inhibit platelet coagulation, they may also be administered for their antiallergic and antithrombotic effects. It has also been discovered that the above compounds and their pharmaceutically acceptable salts are useful as analgesics and anti-pyretics as well as for their inhibitory action against edema.

According to one embodiment of the present invention, the compounds of the present invention are represented by the formula (II):

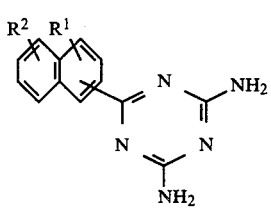

and pharmaceutically acceptable salts thereof wherein $R^1$ and $R^2$ are as above defined. Compounds of the formula (II) can be produced, for example, by reacting known or novel naphthonitriles or naphthoates of the formula (III):

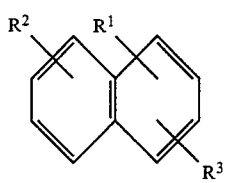

wherein $R^1$ and $R^2$ are as above defined and $R^3$ is -CN or -COOR$^5$ wherein $R^5$ is lower alkyl with cyanoguanidine or biguanide, respectively. The naphthonitriles of the formula (III) can themselves be produced by the following reaction scheme:

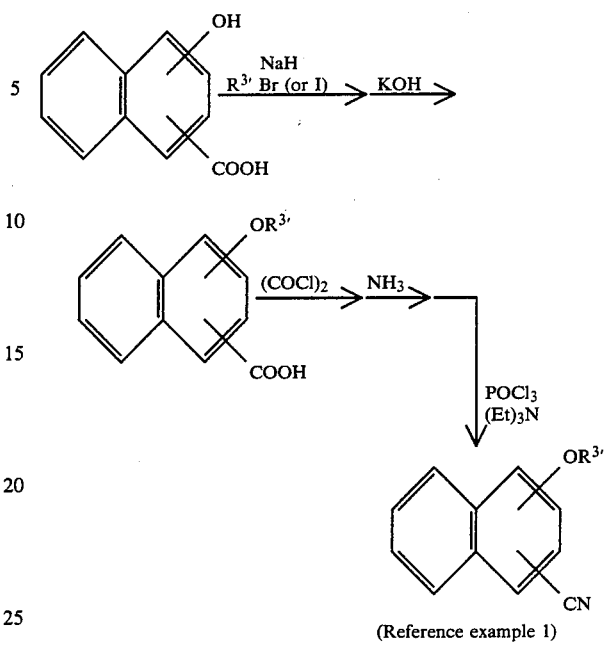

(Reference example 1)

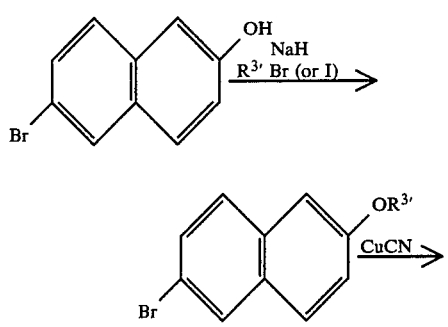

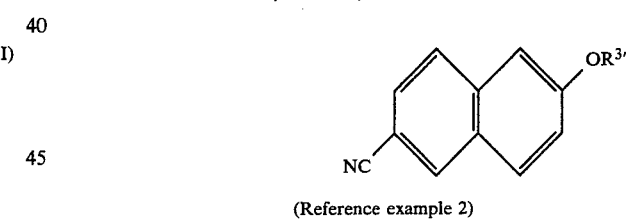

(Reference example 2)

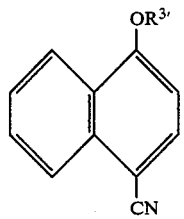

(Reference example 3)

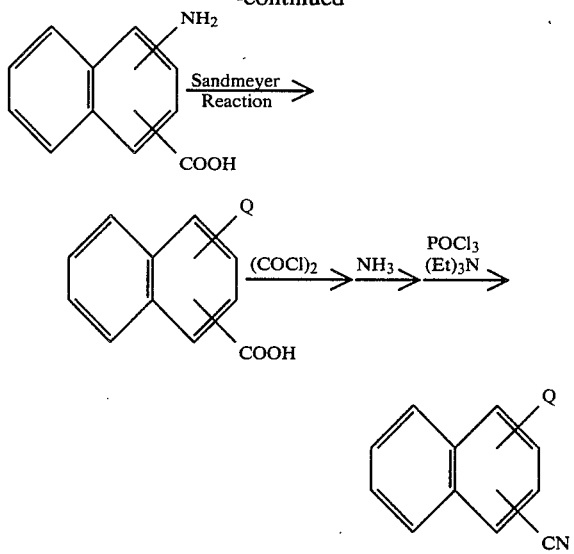

R$^{3'}$ in the above formulae is alkyl or aralkyl and Q is halo.

Naphthonitriles having halo substituents may be produced by synthesizing halo substituted naphthoic acids from the corresponding aminonaphthoic acids according to the procedure described by W. Adcock et al (Aust. J. Chem., 1965, 18, 1351–64) followed by a method set forth in the examples below. Naphthoates can be obtained, inter alia, by esterifying the corresponding carboxylic acids using techniques per se known.

Compounds according to the present invention having nicotinoyl substituents can be produced by reacting a compound of the formula (II) with activated derivatives of nicotinic acid. Examples of such activated derivatives are acid anhydrides, acid chlorides and sulfonic acid anhydrides. When an excess of nicotinic acid reagents are used in this reaction, a considerable amount of the di-nicotinoyl compounds will be produced.

A further embodiment of the present invention comprises compounds of the formula (IV):

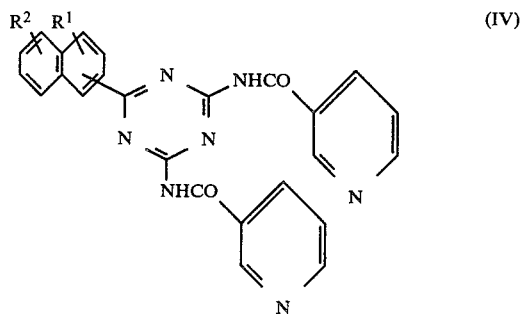

and pharmaceutically acceptable salts thereof wherein R$^1$ and R$^2$ are as above defined. Such compounds can be converted to mononicotinoyl compounds, that is compounds wherein one of X and Y is nicotinoyl in formula (I) by treating compounds of the formula (IV) with various primary or secondary amines or an alcohol such as methyl alcohol.

According to a further embodiment of the present invention, compounds of the formula (I) are produced wherein R$^1$ and R$^2$ are hydrogen, hydroxyl, fluoro, chloro, bromo, alkoxy of 1 or 2 carbon atoms, preferably methoxy, aralkyloxy of 1 or 2 carbon atoms in the alkyl moiety, preferably benzyloxy.

According to a further embodiment of the present invention, R$^1$ is preferably hydrogen, hydroxyl, fluoro, chloro, bromo, methoxy or benzyloxy; R$^2$ is hydrogen, methoxy or benzyloxy; X is hydrogen and Y is nicotinoyl.

Representative compounds according to the present invention are as follows:

2-Amino-4-nicotinoylamino-6-beta-naphthyl-s-triazine; 2,4-diamino-6-(2-benzyloxy-1-naphthyl)-s-triazine; 2,4-diamino-6-(1-benzyloxy-2-naphthyl)-s-triazine; 2,4-diamino-6-(2-benzyloxy-3-naphthyl)-s-triazine; 2,4-diamino-6-(1-benzyloxy-4-naphthyl)-s-triazine; 2,4-diamino-6-(2-methoxy-naphthyl)-s-triazine; 2,4-diamino-6-(1-methoxy-2-naphthyl)-s-triazine; 2,4-diamino-6-(2-methoxy-3-naphthyl)-s-triazine 2,4-diamino-6-(1-methoxy-4-naphthyl)-s-triazine; 2-amino-4-nicotinamido-6-(1-methoxy-4-naphthyl)-s-triazine; 2,4-dinicotinoylamino-6-(2-methoxy-3-naphthyl)-s-triazine; 2,4-diamino-6-(2-methoxy-6-naphthyl)-s-triazine; 2-amino-4-nicotinamido-6-(2-methoxy-3-naphthyl)-s-triazine; 2-amino-4-nicotinamido-6-(2-methoxy-6-naphthyl)-s-triazine; 2-amino-4-nicotinamido-6-(2-benzyloxy-1-naphthyl)-s-triazine; 2,4-dinicotinoylamino-6-(2-chloro-3-naphthyl)-s-triazine; 2-amino-4-nicotinamido-6-(1-benzyloxy-4-naphthyl)-s-triazine; 2-amino-4-nicotinamido-6-(1-hydroxy-2-naphthyl)-s-triazine; 2,4-diamino-6-(2-benzyloxy-6-naphthyl)-s-triazine; 2,4-dinicotinoylamino-6-beta-naphthyl-s-triazine; 2,4-diamino-6-(2-fluoro-3-naphthyl)-s-triazine; 2,4-diamino-6-(2-chloro-3-naphthyl)-s-triazine; 2,4-diamino-6-(2-bromo-3-naphthyl)-s-triazine; 2,4-diamino-6-(1-chloro-4-naphthyl)-s-triazine; 2,4-diamino-6-(1-bromo-4-naphthyl)-s-triazine; 2,4-dinicotinoylamino-6-(2-fluoro-3-naphthyl)-s-triazine; 2-amino-4-nicotinamido-6-(2-fluoro-3-naphthyl)-s-triazine; 2-amino-4-nicotinamido-6-(2-chloro-3-naphthyl)-s-triazine; 2-amino-4-nicotinamido-6-(2-bromo-3-naphthyl)-s-triazine; 2-amino-4-nicotinamido-6-(1-chloro-4-naphthyl)-s-triazine; 2-amino-4-nicotinamido-6-(1-bromo-4-naphthyl)-s-triazine; or 2-amino-4-nicotinamido-6-(6-benzyloxy-2-naphthyl)-s-triazine.

The following test procedures were employed to demonstrate that the compounds of the present invention exhibit carrageenin edema inhibitory action.

TEST METHOD

Five male rats (SLC-SD strain, five weeks age, supplied by Seidokyo) were used in one group in the experiment. Drugs to be tested were given orally at a dose of 400 mg/kg and, one hour later, 0.1 ml of 0.5% carrageenin was injected subcutaneously to right hind paw. Three hours later, volumes of the right hind paws were measured, volumes of the paws before the carrageenin injection were deducted therefrom, and the resulting volumes were defined as a degree of swelling.

The inhibitory rates were calculated from mean degree of swelling of the drug-administered groups and the control group and the result in shown in Table 1.

TABLE 1

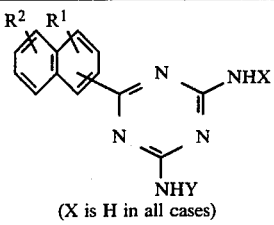

(X is H in all cases)

| Example Number | R$^1$ | R$^2$ | Triazine | Y | Carrageenin Edema Inhibitory Rate (%) |
|---|---|---|---|---|---|
| 1 | 2-OCH$_3$ | H | 3 | H | 60.3 |
| 2 | 1-OCH$_3$ | H | 4 | Nicotinoyl | 34.7 |
| 3 | 2-F | H | 3 | Nicotinoyl | 56.5 |
| 5 | 2-OCH$_2$Ph | H | 3 | H | 30.4 |
| 6 | 1-OCH$_2$Ph | H | 4 | H | 30.9 |
| 7 | 2-OCH$_3$ | H | 1 | H | 44.6 |
| 9 | 1-OCH$_3$ | H | 4 | H | 52.4 |
| 10 | H | 2-OCH$_2$Ph | 6 | H | 50.3 |
| 11 | 2-F | H | 3 | H | 48.8 |
| 12 | 2-Cl | H | 3 | H | 61.3 |
| 13 | 2-Br | H | 3 | H | 49.1 |
| 14 | 1-Cl | H | 4 | H | 42.6 |
| 15 | 1-Br | H | 4 | H | 48.4 |
| 16 | H | 2-OCH$_3$ | 6 | H | 51.1 |
| 18 | H | H | 2 | Nicotinoyl | 24.8 |
| 19 | 2-OCH$_3$ | H | 3 | Nicotinoyl | 35.0 |
| 23 | H | 6-OCH$_2$Ph | 2 | Nicotinoyl | 28.1 |
| 24 | 1-Cl | H | 4 | Nicotinoyl | 25.0 |
| 25 | 1-Br | H | 4 | Nicotinoyl | 25.1 |
| 27 | 2-Br | H | 3 | Nicotinoyl | 33.5 |
| 28 | 1-OH | H | 2 | Nicotinoyl | 19.4 |

In the above table, the figures under R$^1$, R$^2$ and "Triazine" indicate the positions of each substituent on the naphthalene ring.

Acute toxicity studies were performed on compounds 1, 2, 3, 9, 12, 18, 23, 24 and 28 according to the present invention and after oral administration of 2000 mg/kg of said compounds to male mice, no toxicity was observed.

According to a further embodiment of the present invention, pharmaceutical compositions are produced by combining a therapeutically effective amount of a compound of the formula (I) and a pharmaceutically acceptable salt thereof with a pharmaceutically acceptable carrier.

The present invention also includes methods of treating edema, inflammation, pain, fever, allergies and thrombosis in humans and animals which comprises administering a therapeutically effective amount of a compound of the formula (I) or a pharmaceutically acceptable salt thereof, in combination with a pharmaceutically acceptable carrier.

Suitable pharmaceutical compositions according to the present invention may contain from 0.1% to 99.5% of a compound of the formula (I) or a pharmaceutically acceptable salt thereof or more preferably from about 0.5% to about 90%. Such pharmaceutical compositions are preferably in dosage unit form; i.e., physically discrete units containing a predetermined amount of the compound of the formula (I) or a pharmaceutically acceptable salt thereof corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day.

Although the dosage and dosage regimen must in each case be carefully adjusted, utilizing sound professional judgment and considering the age, weight and condition of the recipient, the route of administration and the nature and gravity of the illness, generally the dosage for an average human will be as follows: for oral administration from about 50 to about 3000 mg one to three times per day of said compound or salt thereof for an average adult. For parenteral administration, from about 1 to about 1000 mg three to four times per day. For rectal administration, from about 1 to about 1000 mg one to three times per day. For inhalation and nasal administration, from about 0.1 to about 300 mg two to three times per day. For topical application such as ointment, from about 1 to about 300 mg two to three times per day. In some instances, a sufficient therapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitable comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating,, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds and pharmaceutically acceptable salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccarin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

The compositions of the present invention can be rectally administered in suppository form by mixing a compound of the present invention with a low-melting and water-soluble or insoluble solid such as, for example, polyethylene glycol, cacao fat, higher ester (e.g. myristyl palmitate) or a mixture thereof according to techniques per se known in the art for formulating suppositories.

The compositions of the present invention may also contain other pharmaceuticals such as nonstereoidal analgesics and anti-inflammatory agents, for example, acetylsalicylic acid, indomethacin and phenylbutazone.

The following non-limitative examples more particularly illustrate the present invention:

DESCRIPTION 1

Synthesis of 2-methoxy-3-naphthonitrile

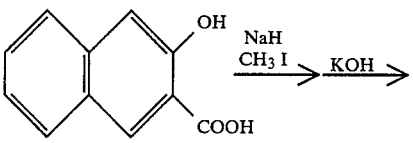

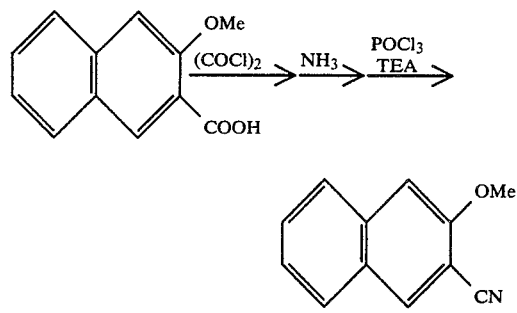

Five grams of 2-hydroxy-3-naphthoic acid was dissolved in 220 ml of dimethyl formamide, 3.74 grams of sodium hydride was added thereto little by little with ice cooling and stirring, then 11.0 grams of methyl iodide was added, and the mixture was stirred at room temperature for twelve hours. The reaction solution was partitioned between benzene and water, the benzene layer was collected, dried over anhydrous magnesium sulfate, the solvent was evaporated therefrom, and the residue was dried. To this were added 10 ml of water, 90 ml of methyl cellosolve and 5.0 grams of potassium hydroxide, the mixture was heated to reflux for forty minutes with stirring, the reaction solution was poured over ice water, the mixture was acidified with diluted hydrochloric acid, and the separated mass was extracted with ethyl acetate. The ethyl acetate extract was dried over anhydrous magnesium sulfate, the solvent was evaporated therefrom, and the residue was crystallized from n-hexane to afford 2-methoxy-3-naphthoic acid. The yield was 4.62 grams.

The resulting 2-methoxy-3-naphthoic acid (4.62 grams) was suspended in 70 ml of anhydrous benzene, heated to reflux with 6.0 ml of oxalyl chloride for thirty minutes, then the solvent was immediately evaporated, and the residue was dried. This was dissolved in 70 ml of anhydrous benzene, ammonia gas was introduced in for ten minutes with ice cooling, the reaction mixture was partitioned between ethyl acetate and water, the ethyl acetate layer was dried with anhydrous magnesium sulfate, the solvent was evaporated, and the residue was dried. To this were added 200 ml of chloroform and 20 ml of triethyl amine, a solution of 7.7 ml of phosphorous oxychloride in 10 ml of chloroform was dropped in with ice cooling and stirring, the mixture was kept at room temperature, and stirred for two hours. The resulting brown solution was poured into ice water, the chloroform layer was taken out, and the chloroform layer was washed with saturated sodium hydrogen carbonate solution and then with water. This was dried with anhydrous magnesium sulfate and the solvent was evaporated therefrom. To the residue was added 50 ml of methyl alcohol, the mixture was heated to reflux for fifteen minutes to decompose the residual phosphorous oxychloride, and methyl alcohol was evaporated therefrom. The resulting residue was subjected to a column chromatography using 120 grams of silica gel and eluted with a mixture of n-hexane and methylene chloride (1:1) to afford 2-methoxy-3-naphthonitrile, colourless crystals, the yield being 3.36 grams.

Infrared absorption spectra (KBr) $\nu C \equiv N$ 2230 cm$^{-1}$.

DESCRIPTION 2

Synthesis of 2-benzyloxy-6-naphthonitrile

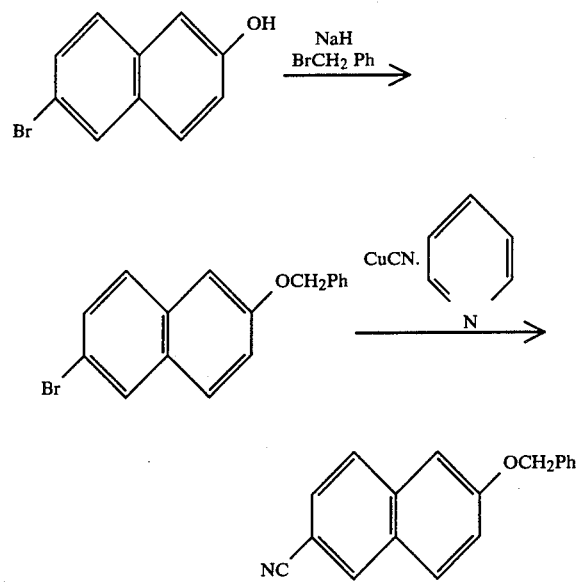

Eight grams of 6-bromo-2-naphthol was dissolved in 200 ml of dimethyl formamide, 2.02 grams of sodium hydride (50%) was added thereto little by little with ice cooling and stirring, then 6.75 grams of benzyl bromide was added, and the mixture was stirred at room temperature for twelve hours. The reaction solution was partitioned between benzene and water, the benzene layer was collected, dried with anhydrous magnesium sulfate, the solvent was evaporated therefrom, and the residue was dried. This was treated with isopropyl alcohol whereupon colourless crystals of 2-benzyloxy-6-bromonaphthalene was obtained. The yield was 10.5 grams.

Ten grams of 2-benzyloxy-6-bromonaphthalene was dissolved in 65 ml of dimethyl formamide, 2.83 grams of cuprous cyanide and 5 to 6 drops of pyridine were added thereto, and the mixture was heated to reflux with stirring for twelve hours. After the reaction was completed, the reaction solution was poured into a mixture of 150 ml of concentrated ammonia water and 150 grams of ice, the mixture was extracted with chloroform, the chloroform extract was washed with diluted hydrochloric acid and then with water, dried with anhydrous sodium sulfate, and the solvent was evaporated therefrom. The resulting residue was subjected to a column chromatography using 200 grams of silica gel and eluted with n-hexane and chloroform mixture (1:1) to afford 2-benzyloxy-6-naphthonitrile, colourless crystals, yield 6.8 grams.

Infrared absorption spectra. (KBr) $\nu$C≡N 2230 cm$^{-1}$.

DESCRIPTION 3

Synthesis of 1-benzyloxy-4-naphthonitrile

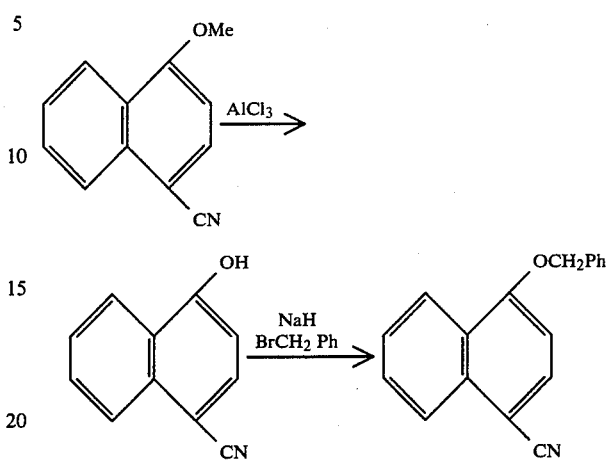

Ten grams of 1-methoxy-4-naphthonitrile was dissolved in 270 ml of benzene, 15.4 grams of aluminum chloride was added thereto, and the mixture was heated to reflux for eighteen hours with stirring. After the reaction was completed, the reaction mixture was partitioned between ethyl acetate and water, the ethyl acetate layer was dried with anhydrous magnesium sulfate, and the solvent was evaporated to afford crude 1-hydroxy-4-naphthonitrile. This was dissolved in 250 ml of dimethyl formamide, 3.39 grams of sodium hydride (50%) was added thereto little by little with ice, cooling and stirring, then 10.21 grams of benzyl bromide was added, and the mixture was stirred for three hours at room temperature. The reaction mixture was subjected to a partition between benzene and water, the benzene layer was dried with anhydrous magnesium sulfate, and the solvent was evaporated therefrom followed by recrystallization of the residue to give 1-benzyloxy-4-naphthonitrile, pale yellow needles, yield 11.85 grams. Nuclear magnetic resonance spectra (CDCl$_3$) $\delta$: 5.20 (2H, s, —CH$_2$—Ph).

EXAMPLE 1

Synthesis of 2,4-diamino-6-(2-methoxy-3-naphthyl)-s-triazine

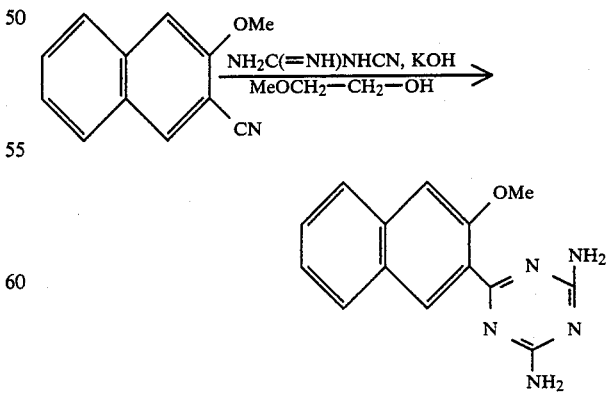

A mixture of 3.24 grams of 2-methoxy-3-naphthonitrile, 2.23 grams of cyanoguanidine and 0.24 gram of KOH was dissolved in 30 ml of methyl cellosolve with heating and the mixture was heated to reflux for 6.5 hours. After the reaction was completed, the reaction solution was was poured into water, the crystals separated out were taken by filtration, and were recrystallized from ethyl alcohol to give 2,4-diamino-6-(2-methoxy-3-naphthyl)-s-triazine, colourless needles, melting point 243° to 244° C., the yield being 4.12 grams.

EXAMPLE 2

Synthesis of 2-amino-4-nicotinoylamino-6-(1-methoxy-4-naphthyl)-s-triazine

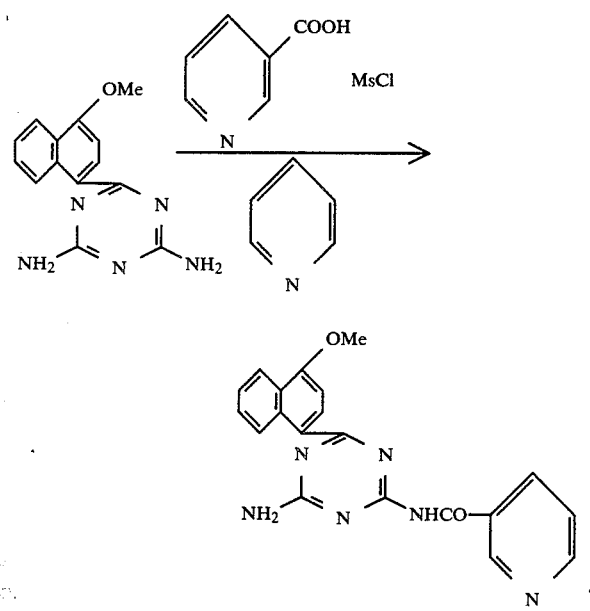

Nicotinic acid (2.98 grams) was dissolved in 40 ml of pyridine, 1.39 grams of methanesulfonyl chloride was added thereto, and the mixture was heated to reflux for thirty minutes. Then 2.7 grams of 2,4-diamino-6-(1-methoxy-4-naphthyl)-s-triazine was added thereto, the mixture was heated to reflux for four hours, and the refluxing was continued for three hours more after addition of 0.35 gram of methane sulfonyl chloride. After the reaction was completed, pyridine was evaporated therefrom, water was added to the residue, the crystals separated out were collected by filtration, well washed with water, added to 130 ml of methyl alcohol, the mixture was heated to reflux for twenty minutes, and the crystals were collected by filtration when the solution was still hot. The crystals were then suspended in 50 ml of methyl alcohol, the suspension was heated to reflux for three hours, and dioxane was added to the suspension to afford 2-amino-4-nicotinoylamino-6-(1-methoxy-4-naphthyl)-s-triazine, beige needles, melting point 208° to 209° C. The yield was 1.84 grams.

Elementary analysis calculated for $C_{20}H_{16}N_6O_2$: C 64.51, H 4.33, N 22.57; Found: C 64.19, H 4.21, N 22.75.

EXAMPLE 3

Synthesis of 2-amino-4-nicotinoylamino-6-(2-fluoro-3-naphthyl)-s-triazine

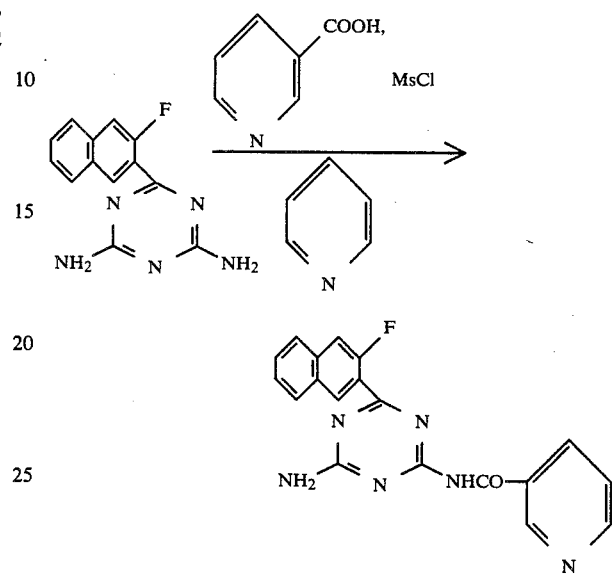

Nicotinic acid (0.58 gram) was dissolved in 10 ml of pyridine, 0.27 gram of methanesulfonyl chloride was added thereto, the mixture was heated to reflux for thirty minutes, 0.5 gram of 2,4-diamino-6-(2-fluoro-3-naphthyl)-s-triazine was added, and the mixture was heated to reflux for four hours. After the reaction was completed, pyridine was evaporated, water was added to the residue, the resulting separated mass was subjected to a column chromatography using 100 grams of silica gel, and eluted with ethyl acetate-benzene (9:1) to afford 2-amino-4-nicotinoylamino-6-(2-fluoro-3-naphthyl)-s-triazine, colourless crystals, melting point 230° to 235° C. (with decomposition). The yield was 0.35 gram.

Elementary analysis calculated for $C_{19}H_{13}FN_6O.1/5-H_2O$: C 62.70, H 3.71, N 23.09; Found: C 62.70, H 3.58, N 23.07.

Similarly prepared were the compounds as listed in the following table starting from the corresponding starting materials.

TABLE 2

(X is H in all cases)

| Example Number | $R^1$ | $R^2$ | Triazine | Y | Melting Point (°C.) |
|---|---|---|---|---|---|
| 4 | 1-OCH$_2$Ph | H | 2 | H | 217–218 |
| 5 | 2-OCH$_2$Ph | H | 3 | H· | 244–245 |
| 6 | 1-OCH$_2$Ph | H | 4 | H | 234–235 |
| 7 | 2-OCH$_3$ | H | 1 | H | 279–280 |
| 8 | 1-OCH$_3$ | H | 2 | H | 170–171 |
| 9 | 1-OCH$_3$ | H | 4 | H | 245 |

TABLE 2-continued

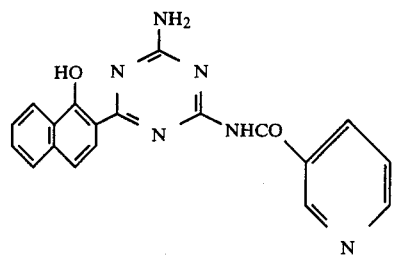

(X is H in all cases)

| Example Number | R¹ | R² | Triazine | Y | Melting Point (°C.) |
|---|---|---|---|---|---|
| 10 | H | 2-OCH₂Ph | 6 | H | 228–229 |
| 11 | 2-F | H | 3 | H | 241–243 |
| 12 | 2-Cl | H | 3 | H | 228–229 |
| 13 | 2-Br | H | 3 | H | 218–219 |
| 14 | 1-Cl | H | 4 | H | 240–241 |
| 15 | 1-Br | H | 4 | H | 218–219 |
| 16 | H | 2-OCH₃ | 6 | H | 248 |
| 17 | 2-OCH₂Ph | H | 1 | H | 114–115 |
| 18 | H | H | 2 | Nicotinoyl | 242–243 |
| 19 | 2-OCH₃ | H | 3 | Nicotinoyl | 237–238 |
| 20 | H | 6-OCH₃ | 2 | Nicotinoyl | 282 |
| 21 | 1-OCH₂Ph | H | 4 | Nicotinoyl | 229–230 |
| 22 | 2-OCH₂Ph | H | 1 | Nicotinoyl | 167–168 |
| 23 | H | 6-OCH₂Ph | 2 | Nicotinoyl | 286–288 |
| 24 | 1-Cl | H | 4 | Nicotinoyl | 205 (decompn) |
| 25 | 1-Br | H | 4 | Nicotinoyl | 155 (decompn) |
| 26 | 2-Cl | H | 3 | Nicotinoyl | 229–230 |
| 27 | 2-Br | H | 3 | Nicotinoyl | 245–247 |

In the table, figures under the items of R¹, R² and "Triazine" show the position of each substituent on the naphthalene ring.

EXAMPLE 28

Synthesis of 2-amino-4-nicotinamido-6-(1-hydroxy-2-naphthyl)-s-triazine

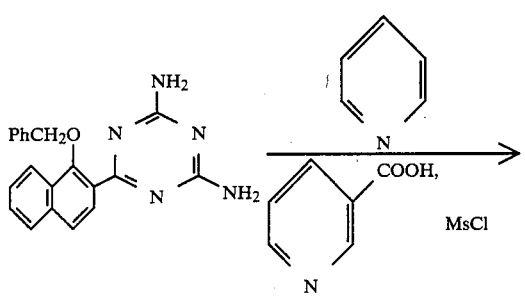

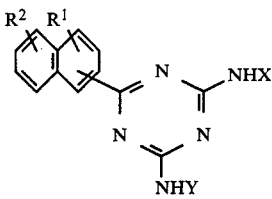

The same methods as in the preceding examples were conducted using 2,4-diamino-6-(1-methoxy-2-naphthyl)-s-triazine or 2,4-diamino-6-(1-benzyloxy-2-naphthyl)-s-triazine to afford 2-amino-4-nicotinamido-6-(1-hydroxy-2-naphthyl)-s-triazine, pale yellow needles, melting point 301° to 302° C.

What we claim is:

1. A method of treating inflammation, pain, fever, allergies and thrombosis in humans and animals which comprises administering to a human or animal in need thereof a therapeutically effective amount of a compound of the formula (I):

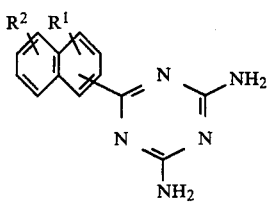

or a pharmaceutically acceptable salt thereof wherein R¹ and R² are the same or different and each is hydrogen, hydroxy, halo, alkoxy of 1 to 4 carbon atoms or aralkyloxy of 1 to 4 carbon atoms in the alkyl moiety wherein the aryl moiety is phenyl; and X and Y are each hydrogen or nicotinoyl provided that at least one of R¹, R², X and Y is other than hydrogen, in combination with a pharmaceutically acceptable carrier.

2. A method according to claim 1 wherein the compound is of the formula (II):

(II)

or a pharmaceutically acceptable salt thereof wherein R¹ and R² are the same or different and each is hydrogen, hydroxy, halo, alkoxy of 1 to 4 carbon atoms or aralkyloxy of 1 to 4 carbon atoms in the alkyl moiety.

3. A method according to claim 1 wherein the compound is of the formula (IV):

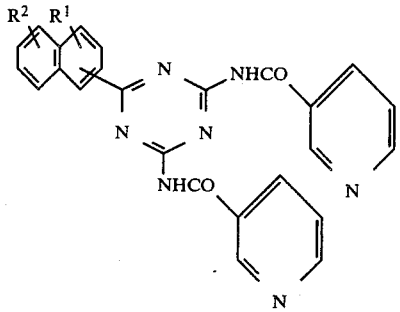

(IV)

or a pharmaceutically acceptable salt thereof wherein R$^1$ and R$^2$ are the same or different and each is hydrogen, hydroxy, halo, alkoxy of 1 to 4 carbon atoms or aralkyloxy of 1 to 4 carbon atoms in the alkyl moiety.

4. A method according to claim 1 wherein R$^1$ and R$^2$ are hydrogen, hydroxy, fluoro, chloro, bromo, methoxy or benzyloxy.

5. A method according to claim 1 wherein R$^1$ is hydrogen, hydroxy, fluoro, chloro, bromo, methoxy or benzyloxy; R$^2$ is hydrogen, methoxy or benzyloxy; X is hydrogen; and Y is nicotinoyl.

6. A method according to claim 1 wherein the compound is
2-Amino-4-nicotinoylamino-6-beta-naphthyl-s-triazine; 2,4-diamino-6-(2-benzyloxy-1-naphthyl)-s-triazine; 2,4-diamino-6-(1-benzyloxy-2-naphthyl)-s-triazine; 2,4-diamino-6-(2-benzyloxy-3-naphthyl)-s-triazine; 2,4-diamino-6-(1-benzyloxy-4-naphthyl)-s-triazine; 2,4-diamino-6-(2-methoxy-1-naphthyl)-s-triazine; 2,4-diamino-6-(1-methoxy-2-naphthyl)-s-triazine; 2,4-diamino-6-(2-methoxy-3-naphthyl)-s-triazine; 2,4-diamino-6-(1-methoxy-4-naphthyl)-s-triazine; 2-amino-4-nicotinamido-6-(1-methoxy-4-naphthyl)-s-triazine; 2,4-dinicotinoylamino-6-(2-methoxy-3-naphthyl)-s-triazine; 2,4-diamino-6-(2-methoxy-6-naphthyl)-s-triazine; 2-amino-4-nicotinamido-6-(2-methoxy-3-naphthyl)-s-triazine; 2-amino-4-nicotinamido-6-(2-methoxy-6-naphthyl)-s-triazine; 2-amino-4-nicotinamido-6-(2-benzyloxy-1-naphthyl)-s-triazine; 2,4-dinicotinoylamino-6-(2-chloro-3-naphthyl)-s-triazine; 2-amino-4-nicotinamido-6-(1-benzyloxy-4-naphthyl)-s-triazine; 2-amino-4-nicotinamido-6-(1-hydroxy-2-naphthyl)-s-triazine; 2,4-diamino-6-(2-benzyloxy-6-naphthyl)-s-triazine; 2,4-dinicotinoylamino-6-beta-naphthyl-s-triazine; 2,4-diamino-6-(2-fluoro-3-naphthyl)-s-triazine; 2,4-diamino-6-(2-chloro-3-naphthyl)-s-triazine; 2,4-diamino-6-(2-bromo-3-naphthyl)-s-triazine; 2,4-diamino-6-(1-chloro-4-naphthyl)-s-triazine; 2,4-diamino-6-(1-bromo-4-naphthyl)-s-triazine; 2,4-dinicotinoylamino-6-(2-fluoro-3-naphthyl)-s-triazine; 2-amino-4-nicotinamido-6-(2-fluoro-3-naphthyl)-s-triazine; 2-amino-4-nicotinamido-6-(2-chloro-3-naphthyl)-s-triazine; 2-amino-4-nicotinamido-6-(2-bromo-3-naphthyl)-s-triazine; 2-amino-4-nicotinamido-6-(1-chloro-4-naphthyl)-s-triazine; 2-amino-4-nicotinamido-6-(1-bromo-4-naphthyl)-s-triazine; or 2-amino-4-nicotinamido-6-(6-benzyloxy-2-naphthyl)-s-triazine.

7. A pharmaceutical composition useful for the treatment of inflammation, pain, fever, allergies and thrombosis in humans and animals which comprises a therapeutically effective amount of a compound of the formula (I):

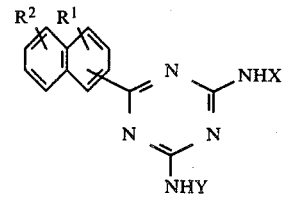

(I)

or a pharmaceutically acceptable salt thereof wherein R$^1$ and R$^2$ are the same or different and each is hydrogen, hydroxy, halo, alkoxy of 1 to 4 carbon atoms or aralkyloxy of 1 to 4 carbon atoms in the alkyl moiety wherein the aryl moiety is phenyl; and X and Y are each hydrogen or nicotinoyl provided that at least one of R$^1$, R$^2$, X and Y is other than hydrogen, in combination with a pharmaceutically acceptable carrier.

8. A composition according to claim 7 wherein the compound is of the formula (II):

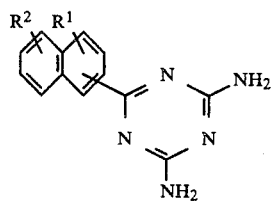

(II)

or a pharmaceutically acceptable salt thereof wherein R$^1$ and R$^2$ are the same or different and each is hydrogen, hydroxy, halo, alkoxy of 1 to 4 carbon atoms or aralkyloxy of 1 to 4 carbon atoms in the alkyl moiety.

9. A composition according to claim 7 wherein the compound is of the formula (IV):

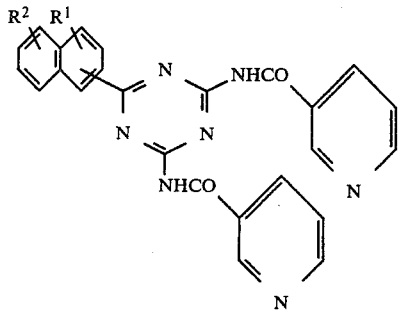

(IV)

or a pharmaceutically acceptable salt thereof wherein R$^1$ and R$^2$ are the same or different and each is hydrogen, hydroxy, halo, alkoxy of 1 to 4 carbon atoms or aralkyloxy of 1 to 4 carbon atoms in the alkyl moiety.

10. A composition according to claim 7 wherein R$^1$ and R$^2$ are hydrogen, hydroxy, fluoro, chloro, bromo, methoxy or benzyloxy.

11. A composition according to claim 7 wherein R$^1$ is hydrogen, hydroxy, fluoro, chloro, bromo, methoxy or benzyloxy; R$^2$ is hydrogen, methoxy or benzyloxy; X is hydrogen; and Y is nicotinoyl.

12. A composition according to claim 7 wherein the compound is
2-Amino-4-nicotinoylamino-6-beta-naphthyl-s-triazine; 2,4-diamino-6-(2-benzyloxy-1-naphthyl)-s-triazine; 2,4-diamino-6-(1-benzyloxy-2-naphthyl)-s- triazine; 2,4-diamino-6-(2-benzyloxy-3-naphthyl)-s-triazine; 2,4-diamino-6-(1-benzyloxy-4-naphthyl)-s-triazine; 2,4-diamino-6-(2-methoxy-1-naphthyl)-s-triazine; 2,4-diamino-6-(1-methoxy-2-naphthyl)-s-triazine; 2,4-diamino-6-(2-methoxy-3-naphthyl)-s-triazine; 2,4-diamino-6-(1-methoxy-4-naphthyl)-s-triazine; 2-amino-4-nicotinamido-6-(1-methoxy-4-naphthyl)-s-triazine; 2,4-dinicotinoylamino-6-(2-methoxy-3-naphthyl)-s-triazine; 2,4-diamino-6-(2-methoxy-6-naphthyl)-s-triazine; 2-amino-4-nicotinamido-6-(2-methoxy-3-naphthyl)-s-triazine; 2-amino-4-nicotinamido-6-(2-methoxy-6-naphthyl)-s-triazine; 2-amino-4-nicotinamido-6-(2-benzyloxy-1-naphthyl)-s-triazine; 2,4-dinicotinoylamino-6-(2-chloro-3-naphthyl)-s-triazine; 2-amino-4-nicotinamido-6-(1-benzyloxy-4-naphthyl)-s-triazine; 2-amino-4-nicotinamido-6-(1-hydroxy-2-naphthyl)-s-triazine; 2,4-diamino-6-(2-benzyloxy-6-naphthyl)-s-triazine; 2,4-dinicotinoylamino-6-beta-naphthyl-s-triazine; 2,4-diamino-6-(2-fluoro-3-naphthyl)-s-triazine; 2,4-diamino-6-(2-chloro-3-naphthyl)-s-triazine; 2,4-diamino-6-(2-bromo-3-naphthyl)-s-triazine; 2,4-diamino-6-(1-chloro-4-naphthyl)-s-triazine; 2,4-diamino-6-(1-bromo-4-naphthyl)-s-triazine; 2,4-dinicotinoylamino-6-(2-fluoro-3-naphthyl)-s-triazine; 2-amino-4-nicotinamido-6-(2-fluoro-3-naphthyl)-s-triazine; 2-amino-4-nicotinamido-6-(2-chloro-3-naphthyl)-s-triazine; 2-amino-4-nicotinamido-6-(2-bromo-3-naphthyl)-s-triazine; 2-amino-4-nicotinamido-6-(1-chloro-4-naphthyl)-s-triazine; 2-amino-4-nicotinamido-6-(1-bromo-4-naphthyl)-s-triazine; or 2-amino-4-nicotinamido-6-(6-benzyloxy-2-naphthyl)-s-triazine.

* * * * *